United States Patent [19]

Raths et al.

[11] Patent Number: 5,292,910

[45] Date of Patent: Mar. 8, 1994

[54] USE OF HYDROPHOBIZED HYDROTALCITES AS CATALYSTS FOR ETHOXYLATION OR PROPOXYLATION

[75] Inventors: Hans-Christian Raths; Wolfgang Breuer; Klaus Friedrich, all of Duesseldorf; Klaus Herrmann, Monheim, all of Fed. Rep. of Germany

[73] Assignee: Henkel Kommanditgesellschaft auf Aktien, Duesseldorf, Fed. Rep. of Germany

[21] Appl. No.: 930,667

[22] PCT Filed: Mar. 25, 1991

[86] PCT No.: PCT/EP91/00566

§ 371 Date: Dec. 2, 1992

§ 102(e) Date: Dec. 2, 1992

[87] PCT Pub. No.: WO91/15441

PCT Pub. Date: Oct. 17, 1991

[30] Foreign Application Priority Data

Apr. 2, 1990 [DE] Fed. Rep. of Germany ....... 4010606

[51] Int. Cl.$^5$ .................... B01J 23/02; C07C 41/03; C07C 43/00; C07C 69/22

[52] U.S. Cl. .................... 554/149; 554/148; 554/154; 568/618; 568/626; 544/401; 558/260; 560/160; 560/179; 502/341

[58] Field of Search ............... 554/148, 149, 153, 154; 568/618, 626; 544/401; 558/260; 560/160, 179; 502/251, 263, 340, 341

[56] References Cited

U.S. PATENT DOCUMENTS

| | | | |
|---|---|---|---|
| 4,299,759 | 11/1981 | Miyata et al. | 260/45 |
| 4,539,195 | 9/1985 | Schanz et al. | 423/419 |
| 4,675,307 | 6/1987 | Taniguchi | 502/341 X |
| 4,902,658 | 2/1990 | King et al. | 502/159 |
| 5,012,012 | 4/1991 | Nakamura et al. | 568/618 |
| 5,064,804 | 11/1991 | Soo et al. | 502/335 |
| 5,104,987 | 4/1992 | King | 544/401 |
| 5,191,104 | 3/1993 | King | 558/260 |

FOREIGN PATENT DOCUMENTS

| | | |
|---|---|---|
| 0082569 | 6/1983 | European Pat. Off. . |
| 0085167 | 8/1983 | European Pat. Off. . |
| 0091146 | 10/1983 | European Pat. Off. . |
| 0092256 | 10/1983 | European Pat. Off. . |
| 0115083 | 3/1986 | European Pat. Off. . |
| 0207811 | 1/1987 | European Pat. Off. . |
| 0339426 | 11/1989 | European Pat. Off. . |
| 1592126 | 10/1970 | Fed. Rep. of Germany . |
| 3019632 | 11/1981 | Fed. Rep. of Germany . |
| 3306822 | 8/1984 | Fed. Rep. of Germany . |
| 3346943 | 7/1985 | Fed. Rep. of Germany . |
| 3833076 | 4/1989 | Fed. Rep. of Germany . |
| 3843713 | 11/1989 | Fed. Rep. of Germany . |

OTHER PUBLICATIONS

Jaocs, vol. 63, 1986, pp. 691-695.
Happi, 1986, pp. 52-54.

*Primary Examiner*—Arthur C. Prescott
*Attorney, Agent, or Firm*—Ernest G. Szoke; Wayne C. Jaeschke; Norvell E. Wisdom, Jr.

[57] ABSTRACT

A process for the catalyzed ethoxylation or propoxylation of compounds selected from the group consisting of organic compounds containing active H atoms, esters of fatty acids containing 2 to 22 carbon atoms with monoalkanols containing 1-22 carbon atoms with polyols containing 2 to 12 carbon atoms and 2 to 6 hydroxyl groups, wherein the improvement comprises the use as catalyst for the ethoxylation or propoxylation of hydrophobicized hydrotalcites corresponding to the general formula I:

$$Mg_xAl(OH)_y(CO_3)_m(A)_n \cdot zH_2O \qquad (I),$$

in which A is selected from the group consisting of (i) a dianion of an aliphatic dicarboxylic acid containing 4 to 44 carbon atoms and (ii) two anions of aliphatic monocarboxylic acids containing 2 to 34 carbon atoms; $1<x<5$; $y \leq 2x+2$; $\{y+2(m+n)\}=2x+3$; $m+n \leq 0.5$; $m \geq 0$; and $0<z<10$.

20 Claims, 8 Drawing Sheets

USE OF HYDROPHOBIZED HYDROTALCITES AS CATALYSTS FOR ETHOXYLATION OR PROPOXYLATION

FIELD OF THE INVENTION

This invention relates to the use of hydrophobicized hydrotalcites corresponding to general formula I:

$$Mg_xAl(OH)_y(CO_3)_m(A)_n \cdot zH_2O \qquad (I),$$

in which A is the dianion of a aliphatic dicarboxylic acid containing 4 to 44 carbon atoms or two anions of aliphatic monocarboxylic acids containing 2 to 34 carbon atoms and the conditions $1<x<5$, $y \geq 2x+2$ $\{y+2(m+n)\}=2x+3$, $m+n \leq 0.5$ $m \geq 0$, $n>0$, and $0<z<10$ apply, as catalysts for the ethoxylation or propoxylation of compounds containing active H atoms and of fatty acid esters selected from the group consisting of esters of optionally hydroxy-substituted fatty acids containing 2 to 22 carbon atoms with monoalkanols containing 1 to 22 carbon atoms and of partial esters and full esters of optionally hydroxy-substituted fatty acids containing 2 to 22 carbon atoms with polyols containing 2 to 12 carbon atoms and 2 to 6 hydroxyl groups.

STATEMENT OF RELATED ART

Hydrotalcite is a natural mineral having the ideal formula $Mg_6Al_2(OH)_{16}CO_3 \cdot 4H_2O$, the structure of which is derived from that of brucite ($Mg(OH)_2$). Brucite crystallizes in a layer structure with the metal ions in octahedral vacancies between two layers of close-packed hydroxyl ions, only every second layer of the octahedral vacancies being occupied. In hydrotalcite, some magnesium ions are replaced by aluminum ions so that the layer packet acquires a positive charge. This is equalized by the anions which are situated in the interlayers together with zeolitic water of crystallization. The layer structure is clear from the X-ray powder diagram (ASTM Card No. 14-191) which may be used for characterization.

Synthetically produced hydrotalcites are also known, cf. for example DE-C 1 592 126, DE-A 3 346 943, DE-A 3 306 822 and EP-A 0 207 811.

In natural and synthetic products, the $Mg^{2+}:Al^{3+}$ ratio can vary between about 1 and 5. The $OH^-:CO_3^{2-}$ ratio can also so vary. Natural and synthetic hydrotalcites can be represented in approximate terms by general formula II:

$$Mg_aAl(OH)_b(CO_3)_c \cdot dH_2O \qquad (II),$$

the conditions $1<a<5$, $b>c$, $(b+2c)=2a+3$, and $0<d<10$ applying. Differences in the composition of the hydrotalcites, particularly in their water content, lead to line shifts in the X-ray diffractogram.

Natural or synthetic hydrotalcites continuously give off water on heating or calcination. The elimination of water is complete at 200° C. It can be shown by X-ray diffraction that the structure of the hydrotalcite is still intact. Any further increase in temperature leads to degradation of the structure with elimination of hydroxyl groups (as water) and carbon dioxide. Natural hydrotalcites and hydrotalcites synthesized by various methods, for example in accordance with the publications cited above, show generally similar behavior on calcination.

Calcined hydrotalcites have already been used with excellent results as ethoxylation and propoxylation catalysts, cf. DE-A 38 43 713. However, they are attended by the disadvantage that they have to be converted from the natural and synthetic hydrotalcites into a calcined form suitable for catalytic purposes by heating for several hours, for example at temperatures of 400° to 600° C.

Hydrophobicized hydrotalcites, in which the carbonate ions are completely or partly replaced by anions of acids, for example even fatty acids, have already been used as stabilizers for thermoplastic resins, cf. DE-C 30 19 632.

DESCRIPTION OF THE INVENTION

SUMMARY OF THE INVENTION

The present invention is based on the discovery that hydrophobicized hydrotalcites are suitable for the ethoxylation or propoxylation of compounds containing active H atoms and of fatty acid esters. This discovery is surprising insofar as untreated natural and synthetic hydrotalcites, i.e. those in non-calcined form, are not active as ethoxylation or propoxylation catalysts.

In the context of the invention, compounds containing active H atoms are, for example, fatty alcohols, fatty acids and amines, which form nonionic detergents on ethoxylation or propoxylation. A typical example of this is the reaction of fatty alcohols typically containing 10 to 18 carbon atoms with ethylene oxide and/or propylene oxide in the presence of catalysts, the fatty alcohols reacting with several molecules of ethylene oxide and/or propylene oxide.

The following catalysts inter alia have been used as catalysts for the above-mentioned polyalkoxylation: calcium and strontium hydroxides, alkoxides, and phenoxides (EP-A 0 092 256), calcium alkoxides (EP-A 0 091 146), barium hydroxide (EP-B 0 115 083), basic magnesium compounds, for example alkoxides (EP-A 0 082 569), magnesium and calcium fatty acid salts (EP-A 0 085 167).

The catalysts mentioned above are attended by the disadvantage inter alia that they do not readily lend themselves to incorporation in the reaction system and-/or are difficult to produce.

Other typical polyalkoxylation catalysts are potassium hydroxide and sodium methylate.

A narrow range of the degree of polyalkoxylation is of particular importance for fatty alcohol polyalkoxylates, cf. JAOCS, vol. 63, 691–695 (1986) and HAPPI, 52–54 (1986). Accordingly, so-called narrow-range alkoxylates have in particular the following advantages:
low flow points,
relatively high smoke points
fewer moles of alkoxide to achieve solubility in water
less hydrotrope for introduction into liquid universal detergents
a weaker odor attributable to the presence of free (unreacted) fatty alcohols
reduction of pluming during spray drying of detergent slurries containing fatty alcohol polyalkoxylate surfactants.

Using hydrophobicized hydrotalcites as catalysts in accordance with the invention, compounds containing active H atoms and fatty acid esters can be polyalkoxylated with high yields in short reaction times. In the same way as the reaction products obtained with calcined hydrotalcites, the reaction products obtained have a narrow homolog distribution range, the distribution curve coming very close to the Poisson curve. The hydrophobicized hydrotalcites used in accordance with the invention have the advantage that they are readily incorporated in the alkoxylation reaction mixture and, by virtue of their insolubility in the reaction mixtures, can be removed again by simple measures. However, they may also remain in the reaction mixture, providing their presence does not interfere with the subsequent use of the reaction products.

DESCRIPTION OF PREFERRED EMBODIMENTS

Examples of compounds which can be alkoxylated in accordance with the invention using hydrophobicized hydrotalcites are given in the following.

Fatty acids

Fatty acids containing 8 to 22 carbon atoms of natural or synthetic origin, more particularly linear, saturated or unsaturated fatty acids, including technical mixtures thereof, which may be obtained by hydrolysis from animal and/or vegetable fats and oils, for example from coconut oil, palm kernel oil, palm oil, soybean oil, sunflower oil, rapeseed oil, cottonseed oil, fish oil, beef tallow, and lard; special examples are caprylic acid, capric acid, lauric acid, lauroleic acid, myristic acid, myristoleic acid, palmitic acid, palmitoleic acid, oleic acid, elaidic acid, arachic acid, gadoleic acid, behenic acid, brassidic acid, and erucic acid; also methyl-branched, saturated and unsaturated fatty acids containing 10 to 22 carbon atoms, which are formed as secondary products in the dimerization of the corresponding unsaturated fatty acids, and monocarboxylic acids containing 1 to 7 carbon atoms.

Hydroxyfatty acids

Natural or synthetic hydroxyfatty acids, more particularly containing 16 to 22 carbon atoms, for example ricinoleic acid or 12-hydroxystearic acid.

Fatty acid amides

Derivatives of the above-mentioned linear, saturated, or unsaturated fatty acids with ammonia or primary aliphatic amines containing 1 to 4 carbon atoms in the aliphatic substituent.

Alkanols

Saturated or unsaturated monoalkanols, more particularly hydrogenation products of the above-mentioned linear, saturated or unsaturated fatty acids or derivatives thereof, such as methyl esters or glycerides; aliphatic or cyclic alkanols containing 2 to 6 carbon atoms, for example ethanol, propanol, butanol, hexanol, and cyclohexanol; including the Guerbet alcohols derived from the monoalkanols mentioned above.

Alkylphenols

Mono-, di- or trialkylphenols, more particularly containing 4 to 12 carbon atoms in the alkyl groups.

Polyglycols

Polyethylene or polypropylene glycols (average degree of polymerization 2 to 2,000).

Fatty amines

Above all primary fatty amines obtainable from nitriles of the linear, saturated, or unsaturated fatty acids mentioned above or the corresponding fatty alcohols; also mono- and di-alkylamines containing $C_{1-6}$ alkyl groups.

Fatty acid alkanolamides

Derivatives of the linear, saturated or unsaturated fatty acids mentioned above with mono- or dialkanolamines, more particularly mono- or di-ethanolamine.

Vicinally hydroxy, alkoxy-substituted alkanes

Ring-opening products of 1,2-epoxyalkane mixtures containing 12 to 22 carbon atoms in the chain with polyfunctional alkanols containing 2 to 12 carbon atoms and 2 to 6 hydroxyl groups; with the proviso for these compounds that they are reacted with ethylene oxide or first with ethylene oxide and then with propylene oxide.

Fatty acid esters

Esters formed from the optionally methyl-branched fatty acids or monocarboxylic acids and hydroxyfatty acids as listed above and the alkanols as listed above; also esters of these acids with polyols, for example with ethylene glycol, 1,2-propylene glycol, 1,2-butylene glycol, neopentyl glycol, glycerol, diglycerol, triglycerol, tetraglycerol, trimethylol propane, ditrimethylol propane, pentaerythritol, dipentaerythritol and sugar alcohols, more particularly sorbitan.

As mentioned at the beginning, esters of the above-mentioned fatty acids with the above-mentioned polyols may also be present in the form of partial esters or technical ester mixtures containing partial esters, more particularly in the form of glycerides.

Preferred fatty acid esters for the ethoxylation and/or propoxylation according to the invention are formed from saturated or unsaturated, optionally methyl-branched or optionally hydroxy-substituted fatty acids containing 8 to 22 carbon atoms with alkanols containing 1 to 4 carbon atoms or with glycerol.

The structure of the ethoxylated or propoxylated fatty acid esters obtained in accordance with the invention is not always clearly discernible. Whereas esters of fatty acids and monoalkanols or full esters thereof would appear to react with polyols with insertion of ethyleneoxy and/or propyleneoxy units into the ester bond, it is not possible to determine which reaction products are formed by the reaction of ethylene oxide and/or propylene oxide with partial esters of fatty acids and polyols or of hydroxy-substituted fatty acids and monoalkanols. Reactions at the free OH groups are also possible in their case, particularly at free primary OH groups.

The derivatives to be produced in accordance with the invention using hydrophobicized hydrotalcites are commercially available products so that there is no need for a detailed account. They are all produced by ethoxylation and/or propoxylation of starting compounds containing active hydrogen atoms or of fatty acid esters. Typical representatives are, for example, an adduct of 9 moles of ethylene oxide with coconut oil fatty acid, an adduct of 2 moles of ethylene oxide with a $C_{12-14}$ fatty alcohol mixture, an adduct of 3 moles of ethylene oxide and 8 moles of propylene oxide with a $C_{12-18}$ fatty alcohol mixture, an adduct of 10 moles of ethylene oxide with nonylphenol, an adduct of 7.3 moles of ethylene oxide with glycerol, an adduct of 10 moles of ethylene oxide with a diol mixture obtained by reaction of a $C_{12-16}$ 1,2-epoxyalkane mixture with ethylene glycol, an adduct of 12 moles of ethylene oxide with a $C_{10-18}$ fatty amine mixture and an adduct of 4 moles of ethylene oxide with coconut oil fatty acid monoethanolamide; also adducts of 41 moles of ethylene oxide with castor oil, adducts of 25 moles of ethylene oxide with hydrogenated castor oil, adducts of 7 parts by weight of ethylene oxide with 10 parts by weight of a palmitic acid/stearic acid mono-/di-glyceride mixture containing 40 to 45% by weight of monoglyceride, and adducts of 20 moles of ethylene oxide with sorbitan monostearate.

In one preferred embodiment of the invention, the hydrophobicized hydrotalcites to be used in accordance with the invention correspond to general formula I, the ratio of m to n being from 92:8 to 0:100 and, more particularly, from 84:16 to 20:80, x, y, z, m, and n being as defined above and the above conditions applying.

The anions A of the monocarboxylic acids which may be used for the hydrophobicization of hydrotalcites to obtain the catalysts to be used in accordance with the invention are, for example, those of the fatty acids mentioned in the foregoing as typical examples of alkoxylated compounds and also, for example, acetic acid, propionic acid, caproic acid, and montanic acid. Typical examples of dicarboxylic acids suitable for the hydrophobicization of hydrotalcites are succinic acid, maleic acid, fumaric acid, adipic acid, pimelic acid, suberic acid, sebacic acid and the like; also so-called dimer fatty acids which may be obtained, for example, from oleic or tall oil fatty acids and contain 36 carbon atoms. The anions A of the hydrophobicized hydrotalcites corresponding to formula I are preferably formed by fatty acids containing 6 to 22 carbon atoms or by dicarboxylic acids, including dimer fatty acids containing 8 to 36 carbon atoms.

Hydrophobicized hydrotalcites corresponding to general formula I which, based on their total weight, contain 5 to 70% by weight and, more particularly, 10 to 55% by weight of the anions A of fatty acids containing 6 to 22 carbon atoms or 10 to 60 and, more particularly, 15 to 50, % by weight of the dianions A of the dicarboxylic acids containing 8 to 36 carbon atoms are also preferred.

The water content of the hydrophobicized hydrotalcites to be used in accordance with the invention may be in the range from 0 to 10, depending on the method of production and the drying conditions. A range of 0 to 4 is preferred and is generally established when the hydrophobicized hydrotalcites are dried to constant weight (about 2 hours) at temperatures in the range from 150° to 220° C.

In another advantageous embodiment of the invention, the compounds containing active H atoms which can be ethoxylated or propoxylated using the hydrophobicized hydrotalcites are selected from the group consisting of fatty acids, hydroxyfatty acids, fatty acid amides, alkanols, alkylphenols, polyglycols, fatty amines, fatty acid alkanolamides, or vicinally hydroxy, alkoxy-substituted alkanols.

In another preferred embodiment, the hydrophobicized hydrotalcites are used in a quantity of 0.1 to 3% by weight, based on the end product of the ethoxylation or propoxylation reaction.

The hydrophobicized hydrotalcites to be used in accordance with the invention may be produced in various ways, for example by reaction of natural or synthetic hydrotalcites with the mono- or di-carboxylic acids in the presence or absence of solvents. In addition, the hydrophobicized hydrotalcites may also be obtained by direct synthesis in the presence of the mono- or dicarboxylic acids under the conditions used for the production of hydrotalcites. Where production is carried out in the absence of air or carbon dioxide, carbonate-free hydrophobicized hydrotalcites corresponding to the above general formula (m=0) are obtained. In the presence of carbon dioxide, carbonate ions are incorporated in the layer structure of the hydrotalcite (m>0). Finally, the hydrophobicized hydrotalcites may also be obtained from calcined hydrotalcite by reaction thereof with the mono- or di-carboxylic acids. As mentioned above, carbonate-free or carbonate-containing products can be obtained in the absence or presence of carbon dioxide. A more detailed account of these production methods is given in connection with the Examples. Using X-ray diffractograms, it can be shown that, in the hydrophobicized hydrotalcites, the hydrotalcite layer structure has remained intact with an increase in the layer spacing.

The invention is illustrated by the following Examples.

The hydrophobicized hydrotalcites to be used in accordance with the invention may be obtained by the following methods:

1. Production in solvents a) 50 g of hydrotalcite (commercially available quality) were suspended in 250 ml of isopropanol and 55 g of oleic acid in 200 ml of isopropanol were added to the resulting suspension over a period of 30 minutes at room temperature (molar ratio of hydrotalcite to oleic acid=1:2).

Heating to the reflux temperature is accompanied by the elimination of $CO_2$. After the elimination of gas has stopped, the reaction mixture is left to react for 1 to 2 hours, cooled, and the suspension is filtered. The filter cake was washed with isopropanol and dried to constant weight in a drying cabinet at 105° C./100 hPa. Yield: 71.5 g; oleic acid content about 40.6% by weight, based on the total weight.

b) A hydrophobicized hydrotalcite was obtained in the same way as described in 1a), except that 33.2 g of lauric acid were used instead of the oleic acid. Yield 56.4%; lauric acid content about 26.4% by weight, based on the total weight; carbonate content 6.9% by weight.

c) A product hydrophobicized with caproic acid is obtained in the same way as described in 1a), except that 19.5 g of caproic acid were used instead of the oleic acid. Yield 67.3 g; caproic acid content about 14.1% by weight, based on the total weight.

d) Hydrophobicization with suberic acid in the same way as described in 1a) produced the required hydrophobicized product. Yield 23.3 g; suberic acid content about 27.4% by weight, based on the total weight.

e) Hydrophobicization with a commercially available C36 dimer fatty acid in the same way as described in 1a) produced the required hydrophobicized product. Yield 29.4 g; dimer fatty acid content about 39.2% by weight, based on the total weight.

f) Hydrophobicization was carried out in the same way as described in 1a), but in water rather than isopropanol as solvent and at a temperature of 80° C. Yield 85.1 g; lauric acid content about 37.6% by weight, based on the total weight.

2. Direct reaction in a kneader (in the absence of solvent)

a) 50 g of commercially available hydrotalcite were processed with 5 g of lauric acid for 1 h at 80° C. in a laboratory kneader. After cooling, the hydrophobicized hydrotalcite is obtained in the form of a powder. Lauric acid content about 9.1% by weight, based on the total weight.

b) A hydrophobicized hydrotalcite powder is obtained in the same way as described in 2a) using 5 g of behenic acid instead of the lauric acid. Behenic acid content about 9.0% by weight, based on the total weight.

Hydrophobicized hydrotalcites containing up to 70% by weight lauric acid or behenic acid can also be obtained by this variant of the process.

3. Direct synthesis of the hydrophobicized hydrotalcites a) Conventional precipitation.

A solution of 77.0 g of $Mg(NO_3)_2.6H_2O$ and 37.5 g of $Al(NO_3)_3.9H_2O$ in 300 ml of water was added dropwise over a period of 90 minutes to solutions of 65 g of 50% sodium hydroxide and I. 40.4 g of sodium oleate,
II. 22 g of sodium laurate, and
III. 13.8 g of sodium caproate in 400 ml water. A colorless precipitate was formed. The suspension was stirred for 15 h at 70° C. After filtration and washing with water, the precipitates obtained were dried in a drying cabinet at 105° C./100 hPa. Yields and analyses:

I.: 54.2 g, oleic acid content about 53.5% by weight; carbonate content: 1.3% by weight II.: 45.1 g, lauric acid content about 38.6% by weight; carbonate content: 1.3% by weight III.: 36.8 g, caproic acid content about 10.7% by weight; carbonate content: 2.9% by weight.

b) Flash precipitation

Solutions of 307.7 g of $Mg(NO_3)_2.6H_2O$ and 150.0 g of $Al(NO_3)_3.9H_2O$ in 8 l of water were pumped through a Y-piece and reacted with solutions of 300 g of 50% sodium hydroxide and I. 136.2 g of behenic acid,
II. 113.0 g of oleic acid,
III. 80.1 g of lauric acid, and
IV. 143.0 g of technical rapeseed oil fatty acid (commercially available) in 8 liters of water. Colorless suspensions were formed and were filtered and washed. The hydrophobicized hydrotalcites obtained were dried in a drying cabinet at 110° C./100 hPa.

Yields and analyses

I.: 256.8 g, behenic acid content about 50.9% by weight;
II.: 230.7 g, oleic acid content about 48.3% by weight;
III.: 172.5 g, lauric acid content about 33.7% by weight;
IV.: 279.6 g, rapeseed oil fatty acid content about 49.7% by weight.

4. Production from calcined hydrotalcite

Hydrotalcite was calcined for 2 h at 500° C. A weight loss of water and carbon dioxide of about 60% by weight occurred.

a) Reaction with sodium laurate 10 g of the calcined hydrotalcite were suspended in 100 ml of water in the presence of air and a solution of 13.3 g of sodium laurate in 100 ml of water was added at room temperature to the resulting suspension. After the entire solution had been added, the suspension was heated for 2 h to 70° C., cooled and filtered. The filter cake was washed with water until the washing water indicated a pH value of 10. The hydrophobicized hydrotalcite was dried to constant weight at 110° C./100 hPa. 22.5 g of a colorless product were obtained; lauric acid content about 38.2% by weight; carbonate content 3.1% by weight.

Repetition of this Example with sodium caproate instead of sodium laurate in the absence of air, i.e. in an inert gas atmosphere ($N_2$), produced a caproate-modified hydrotalcite having a carbonate content of <0.1% by weight.

b) Reaction with lauric acid 20 g of the calcined hydrotalcite described above were suspended in 200 ml of water and a solution of 25 g of lauric acid in 100 ml of isopropanol was added to the resulting solution. The reaction mixture was heated for 3 h to 70° C., cooled and filtered. After the filter cake had been washed with isopropanol, it was dried to constant weight at 110° C./100 hPa. 42.3 g of a colorless product were obtained; lauric acid content about 44.4% by weight.

General procedure for the production of alkoxylates of compounds containing active H atoms using the hydrophobicized hydrotalcites according to the invention:

The compound to be alkoxylated was introduced into a pressure reactor and the hydrophobicized hydrotalcite was added. The reactor was then purged with nitrogen and evacuated for 30 minutes at a temperature of 100° C. The temperature was then increased to 180° C. and the required quantity of ethylene oxide or propylene oxide was introduced under a pressure of 400 to 500 kPa (4–5 bars). On completion of the reaction, the mixture is left to afterreact for 30 minutes. The desired reaction product is obtained after filtration.

EXAMPLES 1 TO 10

Using various hydrophobicized hydrotalcites, $C_{12-14}$ fatty alcohol ethoxylates were produced by addition of 2.5 moles or 3.0 moles of ethylene oxide (EO) per mole of a commercially available $C_{12-14}$ fatty alcohol cut (batch size 300 g of fatty alcohol in each case) in accordance with the procedure described above. The particular hydrophobicized hydrotalcites used and their method of production, the concentration of the catalyst in % by weight, based on expected end product, used in the ethoxylation reaction, the reaction time in h and the hydroxyl values (OHV) of the reaction products by comparison with the theoretically expected hydroxyl values are all shown in Table 1 below. Reference is also made in Table 1 to the accompanying drawings showing the homolog distributions of the particular ethoxylates produced.

EXAMPLES 12 TO 19

Various compounds containing active H atoms were ethoxylated or ethoxylated and then propoxylated by the general procedure mentioned above using catalysts hydrophobicized with lauric acid (produced by method 1a) in accordance with the invention.

Table 2 below shows the particular alkoxylates produced, the concentration of the catalyst used in the reaction mixture, based on expected end product, the reaction time, and the characteristic data of the alkoxylates produced. Table 2 also refers the accompanying drawings showing the homolog distribution of some of the alkoxylates obtained.

TABLE 1

Production of C12/14 fatty alcohol ethoxylates
with 2.5 EO (OHV = 184.6) and 3.0 EO (OHV = 172.6)

| Example No. | Hydrophobicization of the catalyst With: | By method: | Catalyst conc. in % by weight | Reaction time in h | *OHV Actual-Target | Fig. No. |
|---|---|---|---|---|---|---|
| 1 | Lauric acid | 1b | 2.0 | 0.75 | 180.0–184.6 | 1 |
| 2 | Lauric acid | 1b | 0.5 | 1.0 | 185.0–184.6 | 2 |
| 3 | Caproic acid | 1c | 2.0 | 0.75 | 178.3–172.6 | 3 |
| 4 | Oleic acid | 1a | 2.0 | 1.0 | 177.0–172.6 | 4 |
| 5 | Behenic acid | 2 | 0.5 | 4.0 | 184.7–184.6 | 5 |
| 6 | Lauric acid | 1f | 0.5 | 1.75 | 175.0–172.6 | 6 |
| 7 | Lauric acid | 2 | 0.5 | 2.25 | 184.0–184.6 | 7 |
| 8 | Lauric acid | 3 | 0.5 | 1.8 | 174.0–172.6 | 8 |
| 9 | Suberic acid | 1d | 0.5 | 1.0 | 175.3–172.6 | 9 |
| 10 | C36 dimer fatty acid | 1e | 0.5 | 0.75 | 172.1–172.6 | 10 |
| 11 | Acetic acid | 4 | 0.5 | 1.0 | 169.5–172.6 | 11 |

*OHV = hydroxyl value,
EO = ethylene oxide

TABLE 2

Ethoxylation or propoxylation of various H active compounds with a hydrotalcite
hydrophobicized with lauric acid obtained by method 1a

| Example No. | Product | Catalyst conc. in % by weight | Reaction time in h | *Characteristic data (actual–target) | Fig. No. |
|---|---|---|---|---|---|
| 12 | C12/14 Fatty alcohol + 6EO | 0.5 | 1.75 | OHV: 127.0–122.4 | 12 |
| 13 | Cyclohexanol + 3EO | 0.5 | 2.2 | OHV: 237.0–241.4 | 13 |
| 14 | Octanol + 4EO | 0.5 | 1.3 | OHV: 184.0–183.9 | 14 |
| 15 | C12/C18 fatty alcohol + 5EO | 0.5 | 1.3 | OHV: 120–116.9 | 15 |
| 16 | 2-Ethylhexanol + 4EO | 0.5 | 2.2 | OHV: 184.0–183.9 | 16 |
| 17 | Lauric acid + 6EO | 0.5 | 5.5 | SV: 119.0–120.5 | |
| 18 | Diethylene glycol monobutyl either + 8EO + 10PO | 0.5 | 8.0 | OHV: 63.0–51.5 | |
| 19 | Dodecylamine + 12EO | 1.5 | 1.7 | AV: 78.7–82.0 | |

*OHV = hydroxyl value,
SV = saponification value,
AV = amine value
EO = ethylene oxide,
PO = propylene oxide

Figure 1:
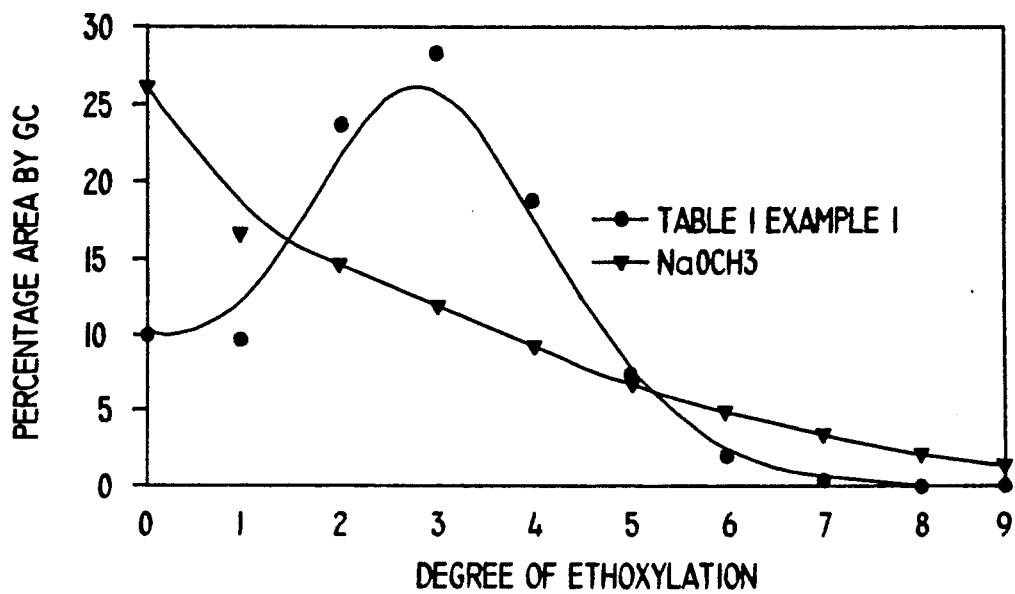
FIGS. 1 to 16 show the homolog distributions obtained for the alkoxylates produced in accordance with the invention. In some cases, the homolog distribution obtained for ethoxylates produced using sodium methylate as ethoxylation catalyst are also shown for comparison purposes. It can be seen that very favorable homolog distributions are obtained where hydrophobicized hydrotalcites are used in accordance with the invention.
Figure 2:
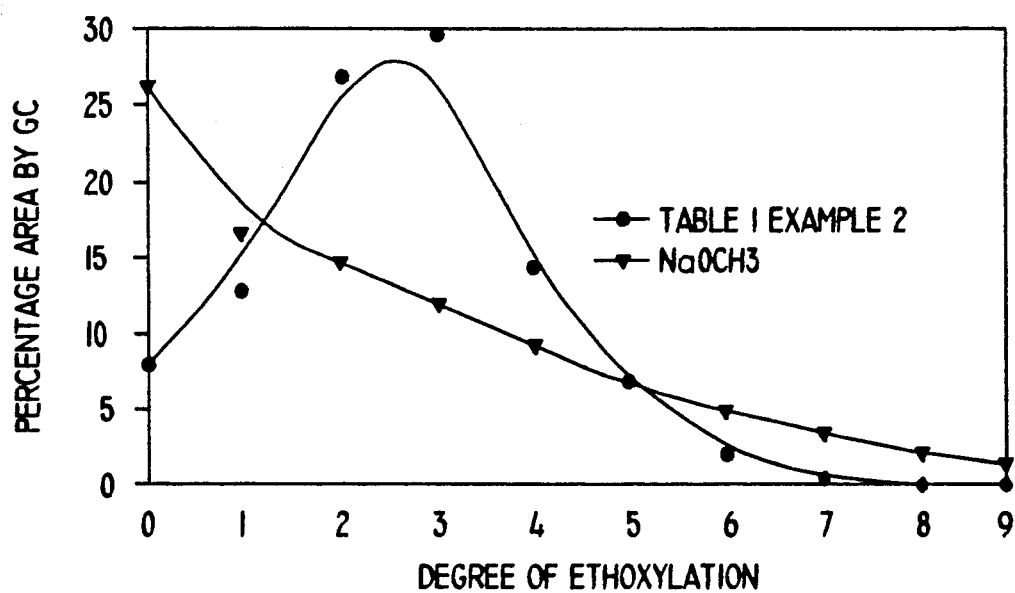
Figure 3:
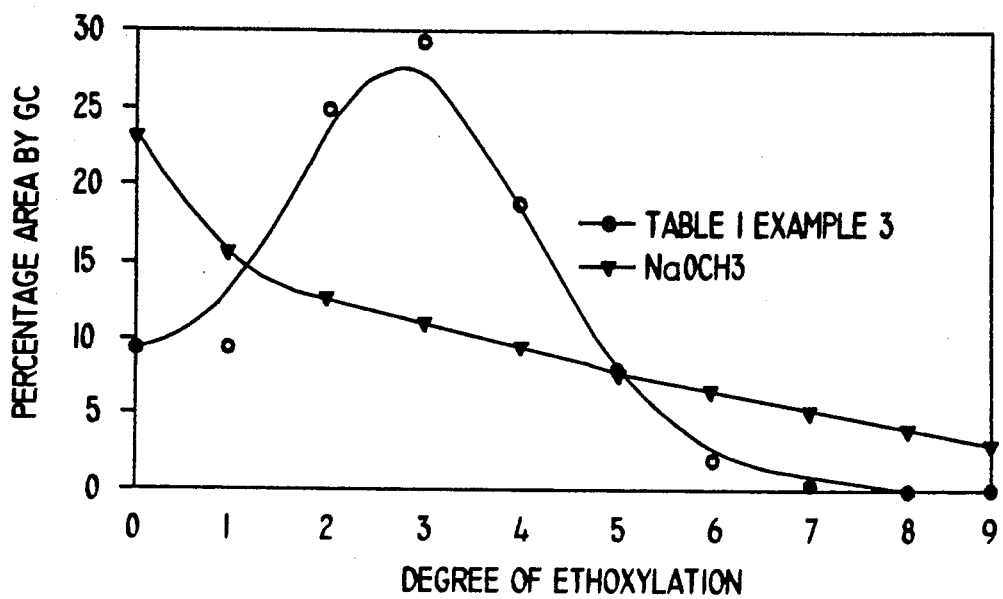
Figure 4:
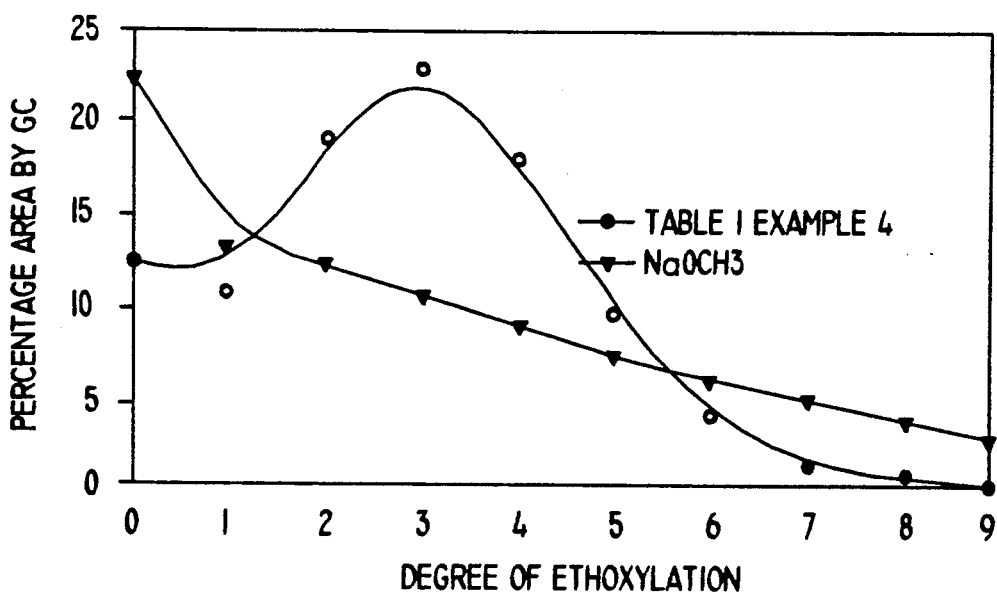
Figure 5:
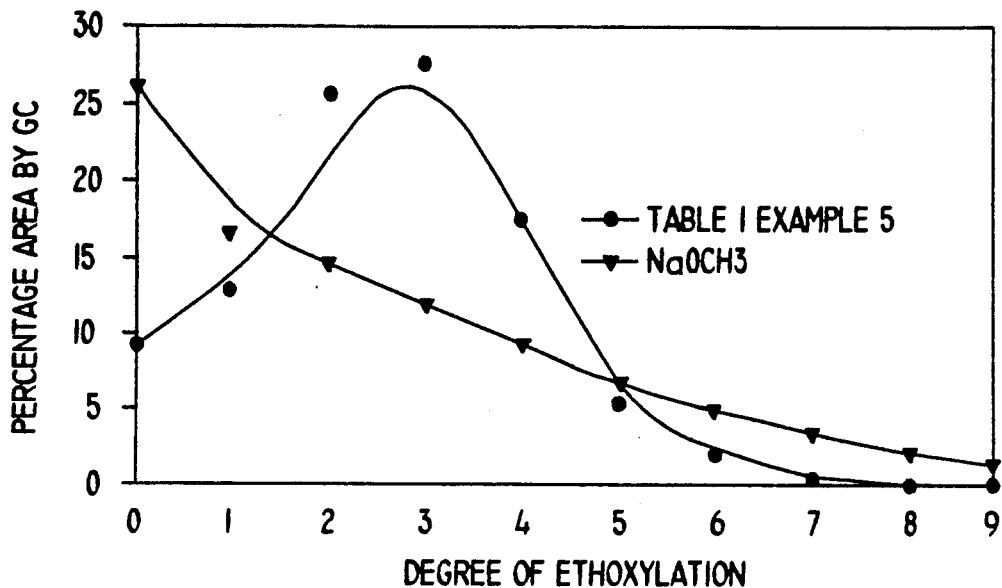
Figure 6:
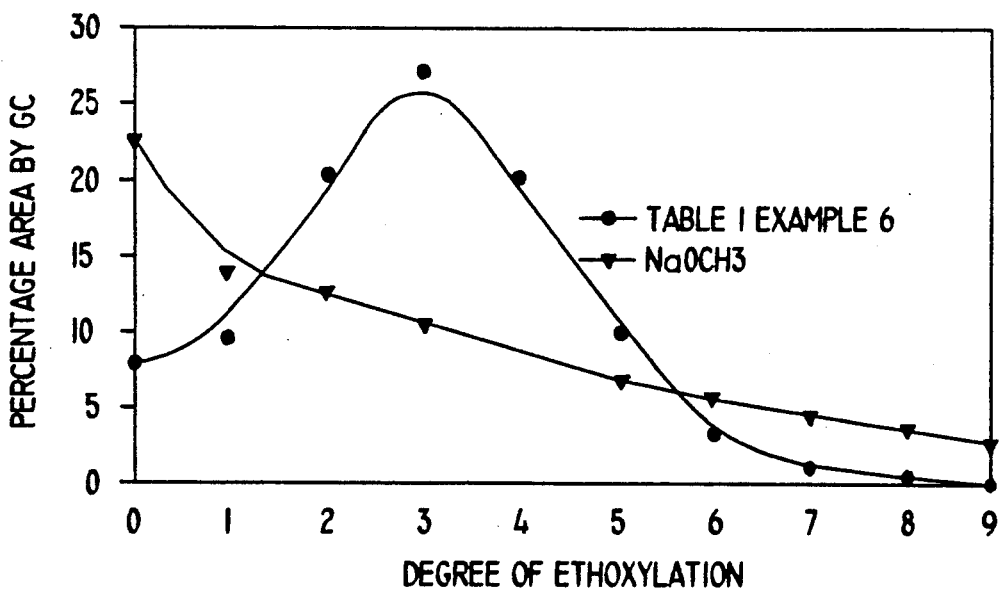
Figure 7:
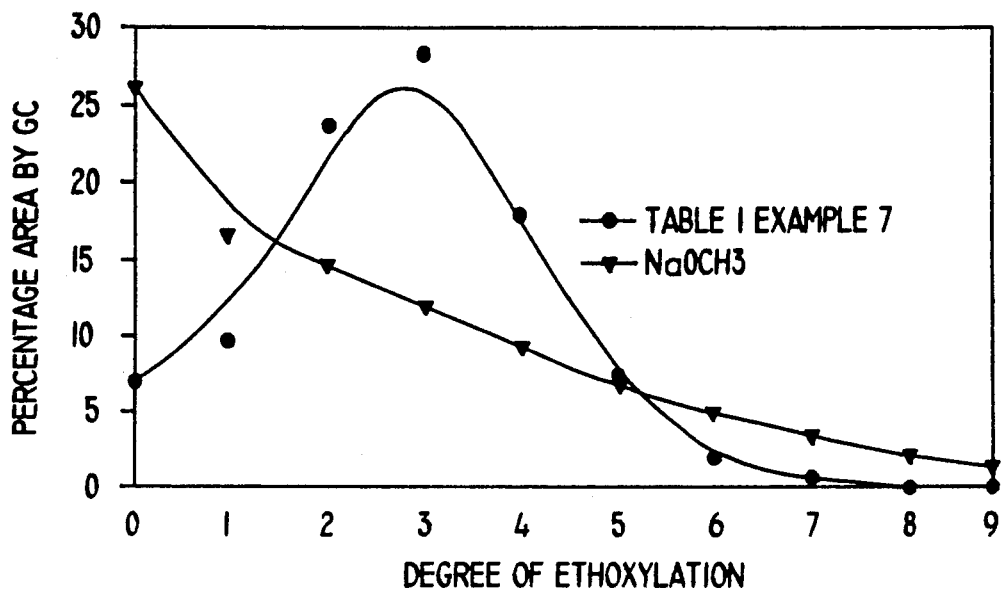
Figure 8:
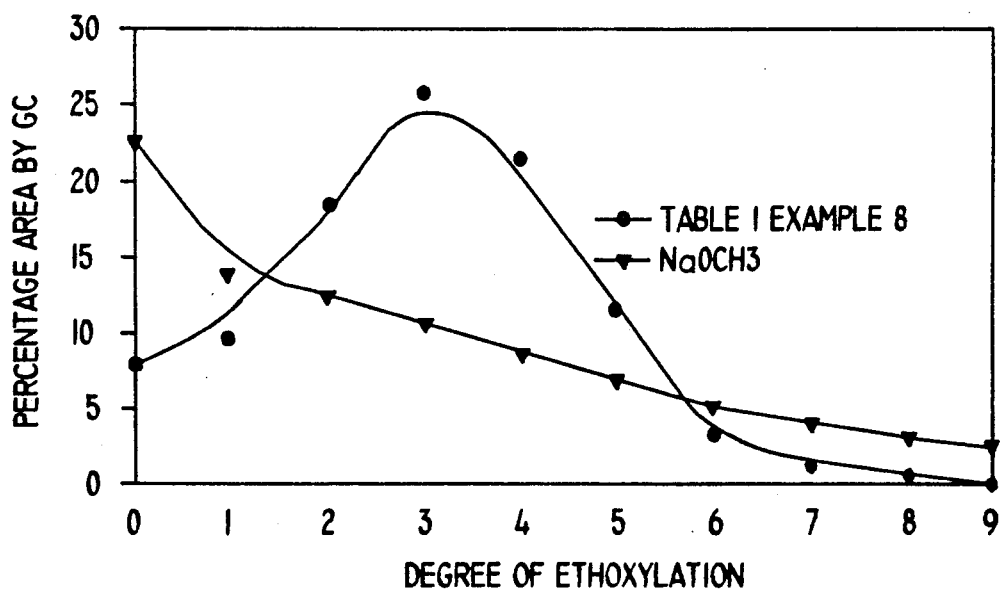
Figure 9:
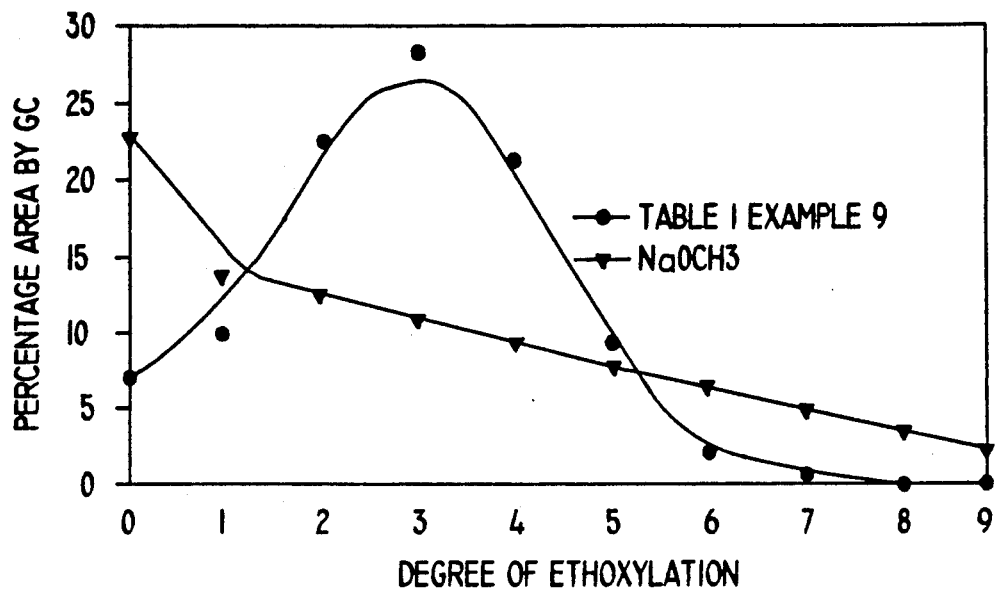
Figure 10:
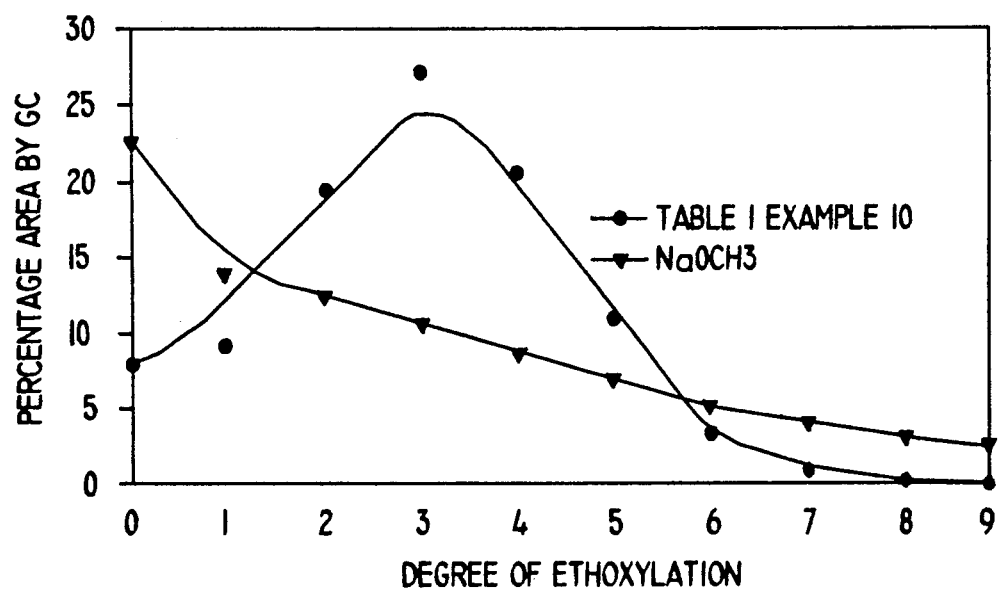
Figure 11:
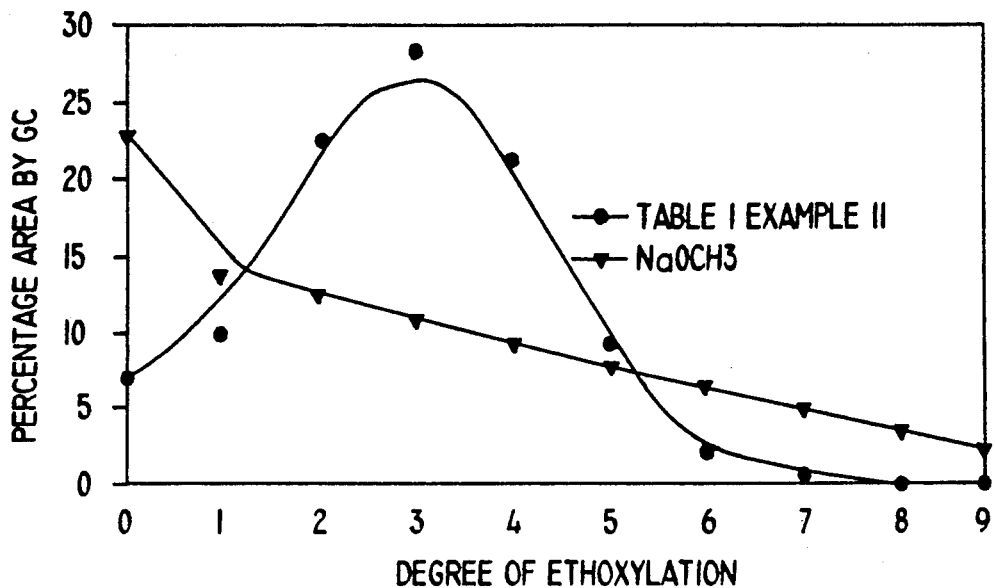
Figure 12:
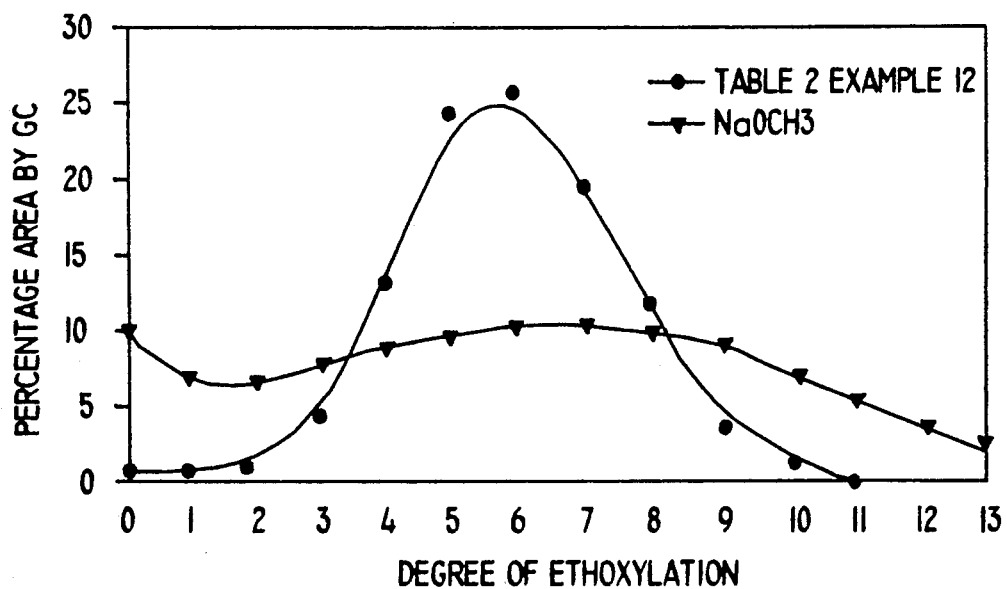
Figure 13:
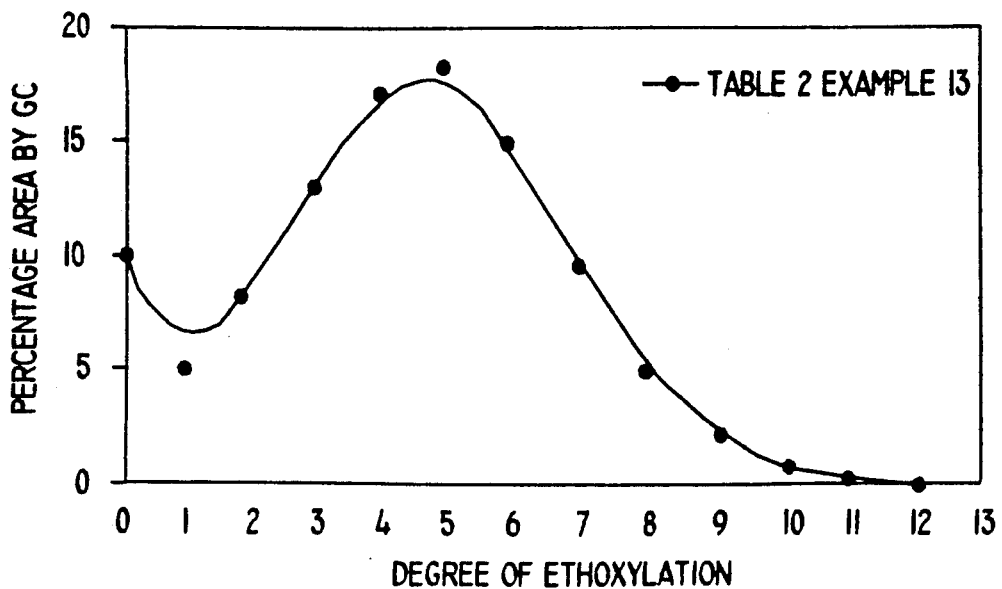
Figure 14:
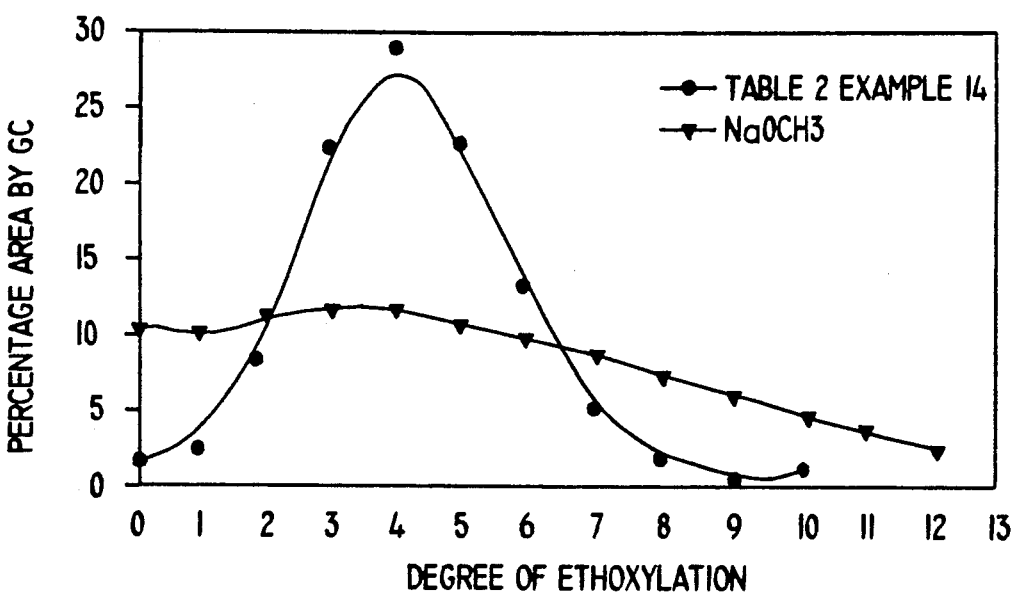
Figure 15:
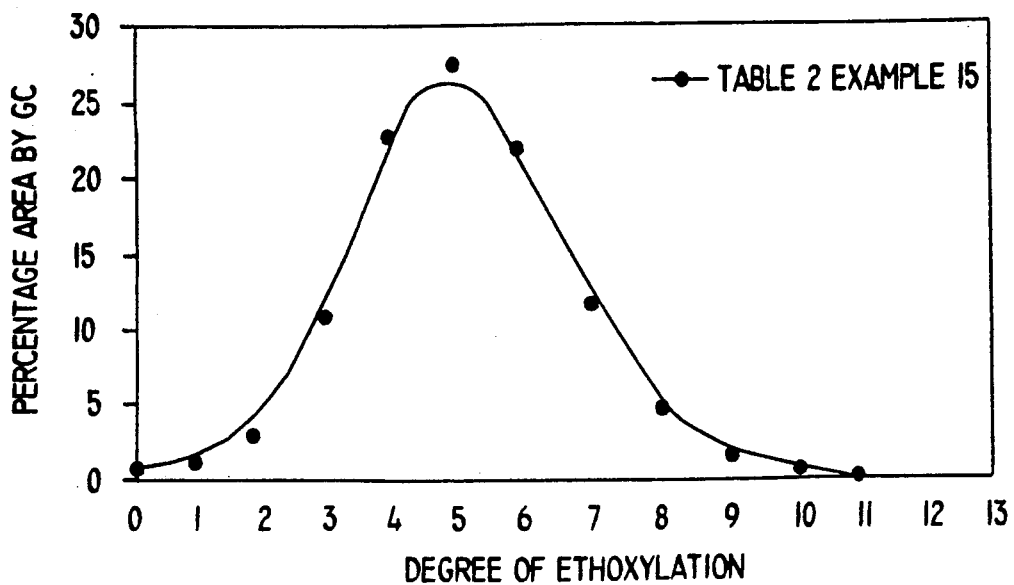
Figure 16:
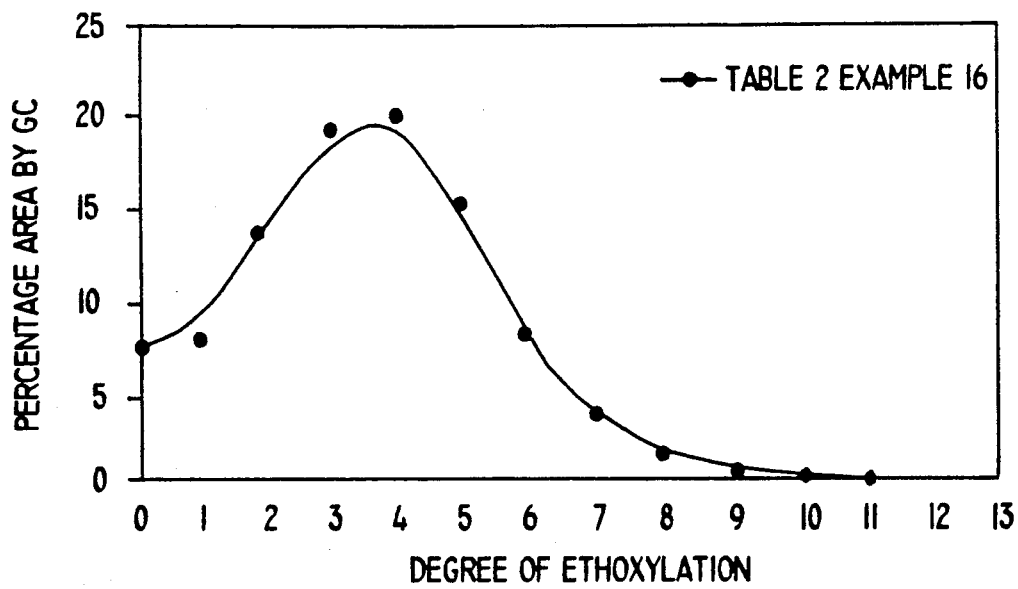

The invention claimed is:

1. A process for the catalyzed ethoxylation or propoxylation of compounds selected from the group consisting of organic compounds containing active H atoms, esters of fatty acids containing 2 to 22 carbon atoms with monoalkanols containing 1 to 22 carbon atoms, and full esters of fatty acids containing 2 to 22 carbon atoms with polyols containing 2 to 12 carbon atoms and 2 to 6 hydroxyl groups, wherein the improvement comprises the use as catalyst for the ethoxylation or propoxylation of hydrophobicized hydrotalcites corresponding to general formula I:

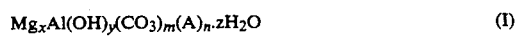

$$Mg_xAl(OH)_y(CO_3)_m(A)_n \cdot zH_2O \quad (I)$$

in which A is selected from the group consisting of (i) a dianion of an aliphatic dicarboxylic acid containing 4 to 44 carbon atoms and (ii) two anions of aliphatic monocarboxylic acids containing 2 to 34 carbon atoms; $1 < x < 5$; $y \leq 2x+2$; $\{y+2(m+n)\} = 2x+3$; $m+n \leq 0.5$; $m \geq 0$; $n > 0$; and $0 < z < 10$.

2. A process as claimed in claim 1, wherein the hydrophobicized hydrotalcites used as the catalyst are selected from those corresponding to general formula I when the ratio of m to n is in the range from 84:16 to 20:80.

3. A process as claimed in claim 2, wherein A is an anion derived from a fatty acid containing 6 to 22 carbon atoms.

4. A process as claimed in claim 3, wherein the hydrophobicized hydrotalcites contain 10 to 55% by weight, based on their total weight, of the anions A of fatty acids containing 6 to 22 carbon atoms.

5. A process as claimed in claim 2, wherein A is a dianion derived from aliphatic dicarboxylic acids, including dimer fatty acids, containing 8 to 36 carbon atoms.

6. A process as claimed in claim 5, wherein the hydrophobicized hydrotalcites contain 15 to 50% by weight, based on their total weight, of the dianions A of aliphatic dicarboxylic acids, including dimer fatty acids, containing 8 to 36 carbon atoms.

7. A process as claimed in claim 6, wherein, in general formula I, z is a number of 0 to 4.

8. A process as claimed in claim 7, wherein the compounds containing active H atoms are selected from the group consisting of fatty acids, hydroxyfatty acids, fatty acid amides, alkanols, alkylphenols, polyglycols, fatty amines, fatty acids alkanolamides, and vicinally hydroxy, alkoxy-substituted alkanols.

9. A process as claimed in claim 8, wherein the hydrophobicized hydrotalcites are used in a quantity of 0.1 to 3% by weight, based on the end product of the ethoxylation or propoxylation reaction.

10. A process as claimed in claim 1, wherein A is an anion derived from a fatty acid containing 6 to 22 carbon atoms.

11. A process as claimed in claim 10, wherein the hydrophobicized hydrotalcites contain 5 to 70% by weight, based on their total weight, of the anions A of fatty acids containing 6 to 22 carbon atoms.

12. A process as claimed in claim 1, wherein A is a dianion derived from an aliphatic dicarboxylic acid, including a dimer fatty acid, containing 8 to 36 carbon atoms.

13. A process as claimed in claim 12, wherein the hydrophobicized hydrotalcites contain 10 to 60% by weight, based on their total weight, of the dianions A of aliphatic dicarboxylic acids, including dimer fatty acids, containing 8 to 36 carbon atoms.

14. A process as claimed in claim 1, wherein in general formula I, z is a number of 0 to 4.

15. A process as claimed in claim 1, wherein the compounds containing active H atoms are selected from the group consisting of fatty acids, hydroxyfatty acids, fatty acid amides, alkanols, alkylphenols, polyglycols, fatty amines, fatty acid alkanolamides, and vicinally hydroxy, alkoxy-substituted alkanols.

16. A process as claimed in claim 7, wherein the hydrophobicized hydrotalcites are used in a quantity of 0.1 to 3% by weight, based on the end product of the ethoxylation or propoxylation reaction.

17. A process as claimed in claim 6, wherein the hydrophobicized hydrotalcites are used in a quantity of 0.1 to 3% by weight, based on the end product of the ethoxylation or propoxylation reaction.

18. A process as claimed in claim 5, wherein the hydrophobicized hydrotalcites are used in a quantity of 0.1 to 3% by weight, based on the end product of the ethoxylation or propoxylation reaction.

19. A process as claimed in claim 4, wherein the hydrophobicized hydrotalcites are used in a quantity of 0.1 to 3% by weight, based on the end product of the ethoxylation or propoxylation reaction.

20. A process as claimed in claim 1, wherein the hydrophobicized hydrotalcites are used in a quantity of 0.1 to 3% by weight, based on the end product of the ethoxylation or propoxylation reaction.

* * * * *